United States Patent
Koga et al.

(10) Patent No.: US 7,229,992 B2
(45) Date of Patent: Jun. 12, 2007

(54) PROCESS FOR THE PREPARATION OF A PIPERAZINE DERIVATIVE

(75) Inventors: Keiichi Koga, Osaka (JP); Ryoki Orii, Osaka (JP); Yosuke Fujii, Osaka (JP); Shunsuke Goto, Osaka (JP); Satoshi Hirabayashi, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 359 days.

(21) Appl. No.: 10/297,592

(22) PCT Filed: Jun. 8, 2001

(86) PCT No.: PCT/JP01/04884

§ 371 (c)(1),
(2), (4) Date: Dec. 13, 2002

(87) PCT Pub. No.: WO01/96332

PCT Pub. Date: Dec. 20, 2001

(65) Prior Publication Data

US 2003/0153753 A1    Aug. 14, 2003

(30) Foreign Application Priority Data

Jun. 13, 2000    (JP)    ............................. 2000-176210

(51) Int. Cl.
*A61K 31/5377*    (2006.01)
*C07D 265/30*    (2006.01)

(52) U.S. Cl. .................................. 514/235.8; 544/106
(58) Field of Classification Search ............. 514/235.8; 544/106
See application file for complete search history.

(56) References Cited

U.S. PATENT DOCUMENTS 5,670,505 A * 9/1997 Matsuo et al. ............... 514/253
5,883,098 A * 3/1999 Matsuo et al. ............... 514/253

FOREIGN PATENT DOCUMENTS

| WO | 96/34864 | 11/1996 |
| WO | 97/08166 | 3/1997 |
| WO | 97/22597 | 6/1997 |
| WO | 98/57954 | 12/1998 |
| WO | WO 9857954 A1 * | 12/1998 |
| WO | 00/35915 | 6/2000 |
| WO | WO 200035915 A1 * | 6/2000 |

* cited by examiner

*Primary Examiner*—Kamal A. Saeed
*Assistant Examiner*—Nyeemah Grazier
(74) *Attorney, Agent, or Firm*—Oblon, Spivak, McClelland, Maier & Neustadt, P.C.

(57) ABSTRACT

(2R)-1-[3,5-bis(trifluoromethyl)benzoyl]-4-[2-[(2S)-2-(methoxymethyl)morpholino]ethyl]-2-(3-hydroxy-4-methylbenzyl)piperazine dihydrochloride is obtained by debenzylating (2R)-4-benzyl-1-[3,5-bis(trifluoromethyl)benzoyl]-2-(3-hydroxy-4-methylbenzyl)piperazine, then N-alkylating and converting to hydrochloride.

12 Claims, 2 Drawing Sheets

PROCESS FOR THE PREPARATION OF A PIPERAZINE DERIVATIVE

This application is a 371 of PCT/JP01/04884, filed on Jun. 8, 2001 and claims benefit to foreign application JAPAN 2000-176210, filed Jun. 13, 2000.

TECHNICAL FIELD

The present invention relates to a novel process for preparing a piperazine derivative represented by the structural formula (I):

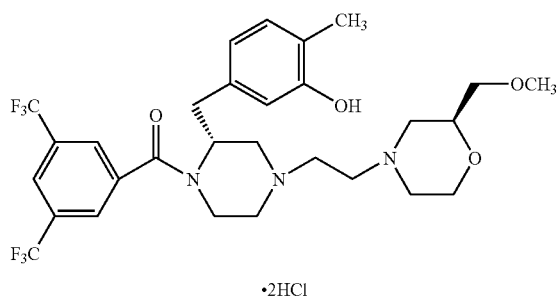

namely, (2R)-1-[3,5-bis(trifluoromethyl)benzoyl]-4-[2-[(2S)-2-(methoxymethyl)morpholino]ethyl]-2-(3-hydroxy-4-methylbenzyl)piperazine dihydrochloride (hereinafter may be abbreviated simply as "Compound I"), which has pharmacological activities such as an antagonism against tachykinin, particularly an antagonism against substance P, an antagonism against neurokinin A, an antagonism against neurokinin B and the like.

BACKGROUND ART

As described in WO 97/22597 A1, WO 98/57954 A1 and WO 00/35915 A1, there have been known several piperazine derivatives having pharmacological activities such as an antagonism against tachykinin and the like.

A problem of the invention is to provide a novel process for preparing a useful piperazine derivative, namely Compound I, which has pharmacological activities such as an antagonism against tachykinin, particularly an antagonism against substance P, an antagonism against neurokinin A, an antagonism against neurokinin B and the like.

DISCLOSURE OF INVENTION

As the result of extensive studies for resolving the above problem, the present inventors have found a method for introducing a side chain into an imino group in (2R)-1-[3,5-bis(trifluoromethyl)benzoyl]-2-(3-hydroxy-4-methyl-benzyl)piperazine, an intermediate within a process for the preparation of Compound I, by selectively alkylating the imino group in the co-existence of the imino group and a phenolic hydroxyl group. According to this method, preparation steps are shortened, operations are simplified and the yield is improved (41.5% by the conventional process vs. 76.7% by the invention process), by omission of a step for introducing once a protective group to the phenolic hydroxyl group, as described in WO 00/35915 A1, and a step for removing said protective group after debenzylating and further reacting (2S)-4-(2-chloro-ethyl)-2-(methoxy-methyl)morpholine or a salt thereof as in steps in the invention.

Consequently, the present invention is directed to a process for preparing (2R)-1-[3,5-bis(trifluoromethyl)-benzoyl]-4-[2-[(2S)-2-(methoxymethyl)morpholino]ethyl]-2-(3-hydroxy-4-methylbenzyl)piperazine dihydrochloride which is characterized by:

(1) a step for debenzylating (2R)-4-benzyl-1-[3,5-bis-(trifluoromethyl)benzoyl]-2-(3-hydroxy-4-methylbenzyl)-piperazine (a compound of the formula (II) shown below) by reduction to produce (2R)-1-[3,5-bis(trifluoromethyl)-benzoyl]-2-(3-hydroxy-4-methylbenzyl)piperazine (a compound of the formula (III) shown below);

(2) a step for subsequently reacting (2R)-1-[3,5-bis-(trifluoromethyl)benzoyl]-2-(3-hydroxy-4-methylbenzyl)-piperazine with (2S)-4-(2-chloroethyl)-2-(methoxymethyl)-morpholine (a compound of the formula (IV) shown below) or a salt thereof in the presence of a base to produce (2R)-1-[3,5-bis(trifluoromethyl)benzoyl]-4-[2-[(2S)-2-(methoxy-methyl)morpholino]ethyl]-2-(3-hydroxy-4-methylbenzyl)-piperazine (a compound of the formula (Ia) shown below), and (3) subsequent conversion of (2R)-1-[3,5-bis(trifluoro-methyl)benzoyl]-4-[2-[(2S)-2-(methoxymethyl)morpholino]-ethyl]-2-(3-hydroxy-4-methylbenzyl)piperazine to hydrochloride.

The invention is shown by a chemical reaction formula as follows:

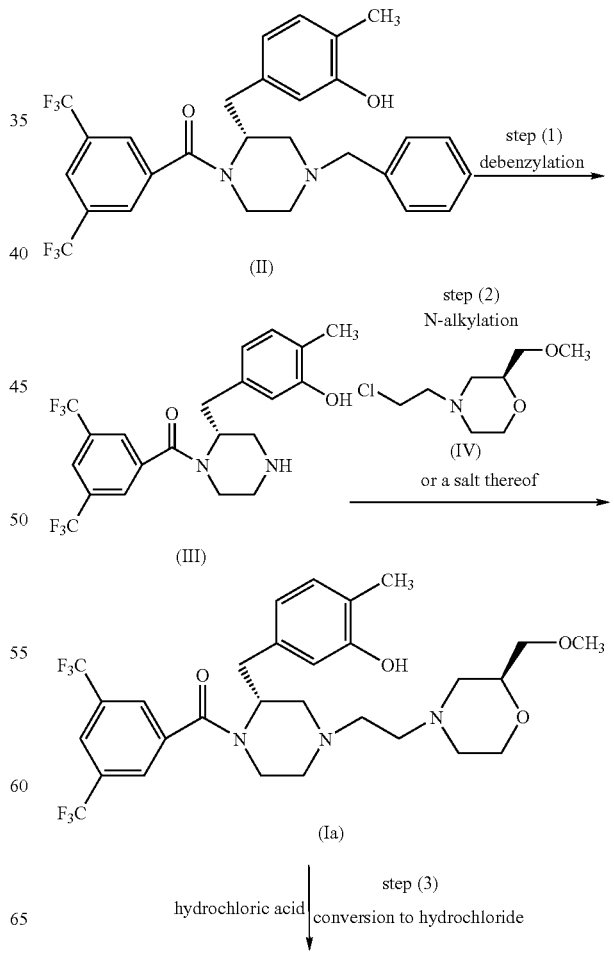

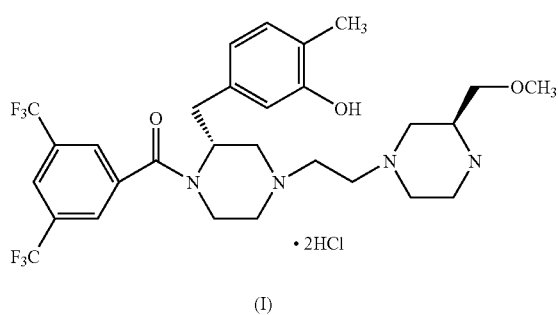

(I)

Preferred salts of (2S)-4-(2-chloroethyl)-2-(methoxymethyl)morpholine are commonly used nontoxic and pharmaceutically acceptable salts, including acid addition salts such as organic acid salts (for example, acetate, trifluoroacetate, fumarate, maleate, tartrate, methane-sulfonate, benzenesulfonate, formate, toluenesulfonate and the like), inorganic acid salts (for example, hydrochloride, hydrobromide, hydroiodide, sulfate, nitrate, phosphate and the like); or salts with amino acids (for example, arginine, aspartic acid, glutamic acid and the like); or alkali metal salts (for example, sodium salt, potassium salt and the like) and alkaline earth metal salts (for example, calcium salt, magnesium salt and the like); ammonium salt; organic base salts (for example, trimethylamine salt, triethylamine salt, pyridine salt, picoline salt, dicyclohexylamine salt, N,N'-dibenzylethylenediamine salt and the like) and others; amongst preferred is hydrochloride.

In the above and following description of the invention, preferred examples and specific examples of various definitions included in the scope of the invention are described below in detail.

Unless particularly specified, "lower" means a number of carbon atoms of 1 to 6, preferably 1 to 4.

Preferred "(lower)alkyl" includes straight chain or branched chain groups such as methyl, ethyl, propyl, isopropyl, butyl, isobutyl, tert-butyl, pentyl, isopentyl, hexyl and the like; amongst preferred is isopropyl.

Embodiments of the process for preparing Compound I according to the invention are described below in detail:

Step (1):

The reduction for debenzylation is effected by commonly used process such as chemical reduction, catalytic reduction and the like.

Preferred reducing agents used in the chemical reduction may include hydrides (for example, hydrogen iodide, hydrogen sulfide, lithium aluminum hydride, sodium borohydride, sodium cyanoborohydride and the like), or combinations of a metal (for example, tin, zinc, iron and the like) or a metal compound (for example, chromium chloride, chromium acetate and the like) with an organic acid or inorganic acid (for example, formic acid, acetic acid, propionic acid, trifluoroacetic acid, p-toluenesulfonic acid, hydrochloric acid, hydrobromic acid and the like).

Preferred catalysts used in the catalytic reduction may include commonly used catalysts such as for example platinum catalysts (for example, platinum plate, platinum sponge, platinum black, colloidal platinum, platinum oxide, platinum wire and the like), palladium catalysts (for example, palladium sponge, palladium black, palladium oxide, palladium on carbon, palladium hydroxide on carbon, colloidal palladium, palladium on barium sulfate, palladium on barium carbonate and the like), nickel catalysts (for example, reduced nickel, nickel oxide, Raney nickel and the like), cobalt catalysts (for example, reduced cobalt, Raney cobalt and the like), iron catalysts (for example, reduced iron, Raney iron, Ullmann iron and the like) and others.

The reaction is usually carried out in a commonly used solvent such as for example water, alcohols (for example, methanol, ethanol, isopropyl alcohol and the like), tetrahydrofuran, dioxane, toluene, methylene chloride, ethylene dichloride, chloroform, N,N-dimethylformamide, N,N-dimethylacetamide and the like, or other organic solvents which do not adversely affect the reaction, or a mixture of them.

Additionally, when the above acids used in the chemical reduction are liquid, these can also be used as solvents. Furthermore, beside hydrogen, a formate (for example, ammonium formate) can also be used in the catalytic reduction.

The temperature for the reduction is not particularly limited and the reaction is usually carried out under cooling to heating (preferably at 40 to 60° C., more preferably at 50 to 55° C.).

Step (2):

The reaction is usually carried out in a commonly used solvent which does not adversely affect the reaction such as for example water, alcohols (for example, methanol, ethanol and the like), acetone, dioxane, acetonitrile, chloroform, methylene chloride, ethylene chloride, tetrahydrofuran, ethyl acetate, N,N-dimethylformamide, pyridine or other organic solvents. These commonly used solvents may be used in mixture with water.

The reaction is carried out in the presence of an inorganicorganicbase, for example, alkalimetalcarbonates (for example, potassium carbonate and the like), alkali metal bicarbonates, tri(lower)alkylamines, pyridine, N-(lower)-alkylmorpholines, N,N-di(lower)alkylethylamines (for example, N,N-diisopropylethylamine and the like), N,N-di(lower)-alkylbenzylamine and the like.

The reaction temperature is not particularly limited and the reaction is usually carried out under cooling to heating (preferably at 40 to 60° C., more preferably at 50 to 55° C.).

Step (3):

The reaction is usually carried out in a commonly used solvent such as for example water, alcohols (for example, methanol, ethanol, isopropyl alcohol and the like), acetone, 2-butanone, dioxane, acetonitrile, chloroform, methylene chloride, ethylene chloride, tetrahydrofuran, ethyl acetate, N,N-dimethylformamide, pyridine, or any other organic solvents which do not adversely affect the reaction, or a mixture of them.

The reaction temperature is not particularly limited and the reaction is usually carried out under cooling, at room temperature or under heating.

After respective reactions are completed, the desired compounds in respective steps are collected from the reaction mixtures by the commonly used methods. For example, the desired compounds can be obtained by clarifying and separating insoluble matters by filtration as necessary when any insoluble matters are present, then adding water to the reaction mixture (after concentration if necessary), extracting the mixture with a water-immiscible solvent such as ethyl acetate, concentrating and drying the extract, and evaporating the solvent; and it is also possible to use the concentrate as it is, obtained by concentrating the above extract, in the next step. Alternatively, the desired compounds may be collected by crystallizing it from the above clarified and filtered reaction mixture with addition of a poor solvent (for example, water and the like). In addition, the conversion to hydrochloride per se in the step (3) is an example of crystallization, and the desired compound can be collected by adding a procedure of cooling crystallization if necessary.

The desired compound collected in this manner is dried by a conventional method, and after drying, it is moisture-conditioned by a conventional method to a desired water content, if necessary.

Additionally, according to the process for preparation of the invention, Compound I, namely (2R)-1-[3,5-bis(trifluoromethyl)benzoyl]-4-[2-[(2S)-2-(methoxymethyl)-morpholino]ethyl]-2-(3-hydroxy-4-methylbenzyl)piperazine dihydrochloride, can be obtained, in one embodiment, in a stable form as sesqui-hydrated (theoretical water content: 3.85%) crystals, as shown in (a) to (c) under (2) of Example 1 described below.

EXAMPLES

The invention is described below in more detail with reference to Preparation Examples and Examples, but the invention is never limited by them.

Preparation Example 1

To a mixed solution of (3R)-3-(methoxymethyl)morpholine hydrochloride (4.71 g) and triethylamine (4.11 ml) in methanol (110 ml) was added 5.8 M ethylene oxide (22 ml) in toluene solution at room temperature. After stirring the reaction mixture at the same temperature for 2 days, the solvent was evaporated under reduced pressure. The residue was purified by silica gel column chromatography using a mixed solvent of dichloromethane and methanol (20:1). Fractions containing the desired compound were collected and the solvent was evaporated under reduced pressure to give 2-[(3R)-3-(methoxymethyl)morpholino]ethanol (4.67 g) in the form of an oily substance.

IR (neat): 3433, 2860, 1454, 1119, 1055 cm$^{-1}$ NMR (CDCl$_3$, δ): 2.38–3.05 (5H, m), 3.33 (3H, s), 3.40–3.80 (8H, m) Mass Analysis (APCI): 176 (M+H)$^+$ Preparation Example 2

Using (2S)-2-(methoxymethyl)morpholine hydrochloride as the starting material, the following compound was obtained in the same manner as that in Preparation Example 1.

2-[(2S)-2-(methoxymethyl)morpholino]ethanol

IR (neat): 3435, 1456, 1354, 1302 cm$^{-1}$ NMR (CDCl$_3$, δ): 2.06 (1H, t, J=10.7 Hz), 2.27 (1H, td, J=10.7 and 3.3 Hz), 2.53–2.58 (2H, m), 2.68–2.84 (2H, m), 3.38 (3H, s), 3.38–3.44 (2H, m), 3.61–3.75 (4H, m), 3.89–3.98 (1H, m) Mass Analysis (API-ES): 176 (M+H)$^+$, 198 (M+Na)$^+$ Preparation Example 3

To an ice-cooled solution of 2-[(3R)-3-(methoxy-methyl)morpholino]ethanol (505 mg) in toluene (2.5 ml) was added dropwise a solution of thionyl chloride (429 mg) in toluene (1.5 ml) at 5° C. or below under a nitrogen atmosphere. The mixture was stirred at 70° C. for 1.5 hours. After cooling the mixture to room temperature, ethyl acetate was added to the mixture and the solvent was evaporated from the produced suspension under reduced pressure. Diisopropyl ether was added to the residue. After stirring the mixture at room temperature for 15 minutes, the produced precipitates were filtered, washed with diisopropyl ether and dried at 40° C. under reduced pressure to give (3R)-4-(2-chloroethyl)-3-(methoxymethyl)morpholine hydrochloride (620 mg) in the form of pale yellow powders.

mp: 162–163° C. IR (KBr): 2945, 1140, 1109, 1084 cm$^{-1}$ NMR (DMSO-d$_6$, δ): 3.31 (3H, s), 3.10–4.10 (13H, m) Mass Analysis (APCI): 194 (M+H)$^+$ (free form compound)

Preparation Example 4

Using 2-[(2S)-2-(methoxymethyl)morpholino]ethanol as the starting material, the following compound was obtained in the same manner as that in Preparation Example 3.

(2S)-4-(2-chloroethyl)-2-(methoxymethyl)morpholine hydrochloride

NMR (DMSO-d$_6$, δ): 3.00 (2H, m), 3.27 (3H, s), 3.47 (4H, m), 3.75–4.12 (7H, m), 11.91 (1H,m) Mass Analysis (APCI): 194 (M+H)$^+$ (free form compound)

Preparation Example 5

In a mixture of water (36.5 ml) and 1N sodium hydroxide solution (29 ml) was dissolved N-acetyl-3-methoxy-4-methyl-DL-phenylalanine (7.28 g). Cobalt chloride (II) hexahydrate (36.5 mg) and acylase (Acylase Amano 36.5 mg) were added to the solution and the mixture was stirred at 37° C. for 15.5 hours while adjusting pH of the reaction mixture to 7.5 with 1N sodium hydroxide solution. Insoluble matters were removed by filtration and pH of the filtrate was adjusted to 3 with 6N hydrochloric acid. After extraction with ethyl acetate, the extract was washed with water, dried over sodium sulfate and the solvent was evaporated under vacuum to give crude N-acetyl-3-methoxy-4-methyl-D-phenylalanine (3.17 g). The crude product was subjected again to the acylase reaction (15.2 mg cobalt chloride (II) hexahydrate, 152 mg acylase, 37° C., pH 7.5, 20 hours) to give pure N-acetyl-3-methoxy-4-methyl-D-phenylalanine (2.70 g) in the form of a viscous oily substance.

$[\alpha]^{26.8}{}_D$: −36.16° (C=0.424, MeOH) IR (neat): 3350, 1740, 1725 cm$^{-1}$ NMR (CDCl$_3$, δ): 1.99 (3H, s), 2.17 (3H, s), 3.00–3.30 (2H, m), 3.78 (3H, s), 4.75–4.90 (1H, m), 6.00–7.10 (3H, m), 6.36 (2H, br s) Mass Analysis (APCI): 252 (M+H)$^+$ Preparation Example 6

A mixture of N-acetyl-3-methoxy-4-methyl-D-phenylalanine (2.55 g) in a mixture of 6N hydrochloric acid (25.5 ml) with toluene (18 ml) was stirred under reflux for 4 hours. After cooling to room temperature, the aqueous layer was separated and the organic layer was washed twice with water (10 ml). The aqueous layer and the washings were combined and the solvent was evaporated under reduced pressure. The produced crystals were collected by filtration and washed with ice-water to give 3-methoxy-4-methyl-D-phenylalanine hydrochloride (1.35 g) in the form of colorless crystals.

The solvent was evaporated from the filtrate under reduced pressure to give crude 3-methoxy-4-methyl-D-phenylalanine hydrochloride (0.6 g).

mp: 207–211° C. $[\alpha]^{27.2}_D$: +20.2° (C=0.5, H$_2$O) IR (KBr): 1735, 1610, 1508 cm$^{-1}$ NMR (D$_2$O, δ): 2.18 (3H, s), 3.17 (1H, dd, J=7.6 and 14.6 Hz), 3.32 (1H, dd, J=6.0 and 14.6 Hz), 3.85 (3H, s), 4.27 (1H, dd, J=6.0 and 7.0 Hz), 6.85 (1H, d, J=7.3 Hz), 6.91 (1H, s), 7.21 (1H, d, J=8.0 Hz) Mass Analysis (APCI): 210 (M+H)$^+$(free form compound)

Preparation Example 7

To a solution of 3-methoxy-4-methyl-D-phenylalanine hydrochloride (1.75 g) in methanol (8 ml) was added dropwise thionyl chloride (0.7 ml) at room temperature over 10 minutes. The total mixture was stirred at 40 to 50° C. for 2 hours and thionyl chloride (0.7 ml) was added further to the mixture. The total mixture was stirred for further 1 hour and the solvent was evaporated under reduced pressure. The produced solid substance was triturated with diisopropyl ether and collected by filtration to give 3-methoxy-4-methyl-D-phenylalanine methyl ester hydrochloride (1.70 g) in the form of colorless crystals.

mp: 196–197° C. $[\alpha]^{30}_D$: −4.60° (C=0.5, MeOH) IR (Nujol): 3400, 1741, S83, 1465, 1446, 1249 cm$^{-1}$ NMR (D$_2$O, δ): 2.19 (3H, s), 3.21 (1H, dd, J=7.4 and 14.5 Hz), 3.32 (1H, dd, J=6.0 and 14.5 Hz), 3.85 (6H, s), 4.43 (1H, dd, J=6.0 and 7.4 Hz), 6.82 (1H, dd, J=1.4 and 7.6 Hz), 6.87 (1H, d, J=1.4 Hz), 7.22 (1H, d, J=7.6 Hz) Mass Analysis (APCI): 224 (M+H)$^+$ (free form compound), 207, 164

Preparation Example 8

To a mixture of 3-methoxy-4-methyl-D-phenylalanine methyl ester hydrochloride (1.60 g) in a mixed solvent of dichloromethane (7 ml) and water (9 ml) was added potassium carbonate (1.70 g) in small portions under ice cooling. Chloroacetyl chloride (0.66 ml) was added to the mixture at 5° C. or below over 15 minutes and then the total mixture was stirred for 30 minutes. The organic layer was separated, washed with an aqueous sodium chloride solution, dried over magnesium sulfate and the solvent was evaporated under reduced pressure to give (2R)-2-[N-(chloroacetyl)amino]-3-(3-methoxy-4-methylphenyl)propionic acid methyl ester in the form of an oily substance.

IR (neat): 3305, 1737, 1643, 1583 cm$^{-1}$

Preparation Example 9

To a solution of (2R)-2-[N-(chloroacetyl)amino]-3-(3-methoxy-4-methylphenyl)propionic acid methyl ester (1.85 g) in N,N-dimethylformamide (15 ml) were added successively benzylamine (1.65 g) and potassium carbonate (1.28 g) at 20° C. After stirring at 35° C. for 1.5 hour, the mixture was poured into a mixture of ice-water (20 ml) and dichloromethane (20 ml). After adjusting the mixture to pH 9 with a diluted aqueous hydrochloric acid solution with stirring, the organic layer was separated, washed with an aqueous sodium chloride solution (20 ml), dried over magnesium sulfate and the solvent was evaporated under reduced pressure to give (2R)-2-[N-(benzylaminoacetyl)amino]-3-(3-methoxy-4-methylphenyl)-propionic acid methyl ester in the form of an oily substance. A solution of (2R)-2-[N-(benzylaminoacetyl)-amino]-3-(3-methoxy-4-methylphenyl)propionic acid methyl ester obtained by the above process and acetic acid (0.18 ml) in isopropyl alcohol (10 ml) was stirred under reflux for 12 hours. After cooling the mixture to room temperature, isopropyl ether was added to the mixture. The produced precipitates were collected by filtration and washed with isopropyl ether to give (3R)-1-benzyl-3-(3-methoxy-4-methylbenzyl)piperazine-2,5-dione (1.45 g) in the form of colorless crystals.

mp: 205–209° C. $[\alpha]^{30}_D$: +11.12° (C=0.4, DMF) IR (KBr): 3237, 1677, 1656, 1465, 1446, 1442 cm$^{-1}$ NMR (DMSO-d$_6$, δ): 2.08 (3H, s), 2.76 (1H, d, J=17.2 Hz), 2.87 (1H, dd, J=4.8 and 13.4 Hz), 3.11 (1H, dd, J=4.8 and 13.4 Hz), 3.46 (1H, d, J=17.2 Hz), 3.69 (3H, s), 4.25 (1H, d, J=14.6 Hz), 4.20–4.30 (1H, m), 4.52 (1H, d, J=14.6 Hz), 6.54 (1H, dd, J=1.4 and 7.4 Hz), 6.69 (1H, d, J=1.4 Hz), 6.87 (1H, d, J=7.4 Hz), 7.04–7.11 (2H, m), 7.24–7.30 (3H, m), 8.33 (1H, d, J=2.2 Hz) Mass Analysis (APCI): 339 (M+H)$^+$ Preparation Example 10

To an ice-cooled suspension of (3R)-1-benzyl-3-(3-methoxy-4-methylbenzyl)piperazine-2,5-dione (1.35 g) in tetrahydrofuran (22 ml) was added lithium aluminum hydride (0.378 g) at 5° C. or below under a nitrogen atmosphere. The mixture was stirred under reflux for 3 hours. After cooling the mixture to 5° C. or below, 2N sodium hydroxide was added to the mixture. After stirring the mixture for 30 minutes, insoluble matters were collected by filtration and washed with tetrahydrofuran. The filtrate and the washings were combined and the solvent was evaporated under reduced pressure to give (3R)-1-benzyl-3-(3-methoxy-4-methylbenzyl)piperazine in the form of an oily substance. A solution of 3,5-bis(trifluoromethyl)benzoyl chloride (0.80 ml) in dichloromethane (1 ml) was added dropwise to an ice-cooled solution of (3R)-1-benzyl-3-(3-methoxy-4-methylbenzyl)-piperazine obtained by the above process and triethylamine (0.84 ml) in dichloromethane (10 ml) at 5° C. or below over 5 minutes. After stirring at the same temperature for 30 minutes, the reaction mixture was washed with an aqueous sodium chloride solution and dried over magnesium sulfate. The solvent was evaporated under reduced pressure. The residue was purified by silica gel column chromatography using a mixed solvent of hexane and ethyl acetate (4:1). Fractions containing the desired compound were collected and the solvent was evaporated under reduced pressure to give (2R)-4-benzyl-1-[3,5-bis(trifluoromethyl)benzoyl]-2-(3-methoxy-4-methylbenzyl)-piperazine (1.92 g) in the form of an oily substance.

IR (neat): 2950, 2850, 1640, 1590, 1515 cm$^{-1}$ NMR (CDCl$_3$, δ): 2.16 (3H, s), 2.00–5.20 (14H, m), 6.25–6.32 (1H, m), 6.70–6.90 (2H, m), 7.20–7.44 (7H, m), 7.80 (1H, br s) Mass Analysis (APCI): 551 (M+H)$^+$, 573 (M+Na)$^+$ Preparation Example 11

To an ice-cooled solution of (2R)-4-benzyl-1-[3,5-bis (trifluoromethyl)benzoyl]-2-(3-methoxy-4-methylbenzyl)-piperazine (0.68 g) in dichloromethane (5 ml) was added dropwise a solution of boron tribromide in dichloromethane (1M solution, 3.7 ml) over 20 minutes. After stirring at the same temperature for 2 hours, the mixture was further stirred at room temperature for 12 hours and poured into a saturated aqueous sodium hydrogen carbonate solution. The organic layer was separated, dried over magnesium sulfate and the solvent was evaporated under reduced pressure. The residue was purified by silica gel column chromatography using a mixed solvent of hexane and ethyl acetate (4:1). Fractions containing the desired compound were collected and the solvent was evaporated under reduced pressure to give (2R)-4-benzyl-1-[3,5-bis(trifluoromethyl)benzoyl]-2-(3-hydroxy-4-methylbenzyl)piperazine (0.56 g) in the form of a red foam substance.

IR (neat): 1630,1430 cm$^{-1}$ NMR (CDCl$_3$, δ): 2.00–5.20 (14H, m), 5.61 (1H, br s), 6.20–6.25 (1H, m), 6.60–7.70 (2H, m), 7.20–7.60 (7H, m), 7.80–7.85 (1H, m) Mass Analysis (API-ES): 519 (M–H$_2$O+H)$^+$, 537 (M+H)$^+$, 559 (M+Na)$^+$ Example 1

(1) Debenzylation

Into a mixed solution of methanol (270 l) and water (30 l) were charged (2R)-4-benzyl-1-[3,5-bis(trifluoromethyl)-benzoyl]-2-(3-hydroxy-4-methylbenzyl)piperazine (30.0 kg), ammonium formate (8.8 kg) and 10% palladium on carbon (wet condition: 50%, 1.5 kg). They were allowed to react at an inside temperature of 50 to 55° C. for 4 hours. After the reaction was completed, the reaction solution was cooled to room temperature, clarified and filtered, and washed with methanol (90 l). Water (480 l) was added dropwise to the combined filtrate and washings at room temperature and crystallization was effected under ice-cooling for 8 hours. Crystals were collected by filtration, washed with water (90 l) and dried under reduced pressure to give (2R)-1-[3,5-bis(trifluoromethyl)benzoyl]-2-(3-hydroxy-4-methylbenzyl)-piperazine (23.7 kg, yield 94.8%) in the form of white crystals.

IR (KBr): 3500–2500, 3300, 1633, 1329, 1192, 1124 cm$^{-1}$ NMR (DMSO-d$_6$, δ): 2.07 (3H, s), 2.5–3.6 (9H, m), 6.1–9.2 (6H, m)

(2) N-alkylation and Conversion to Hydrochloride (a) Into N,N-dimethylformamide (33.5 ml) were charged (2R)-1-[3,5-bis(trifluoromethyl)benzoyl]-2-(3-hydroxy-4-methylbenzyl)piperazine (6.7 g), potassium iodide (8.0 g), (2S)-4-(2-chloroethyl)-2-(methoxymethyl)morpholine hydrochloride (4.3 g) and N,N-diisopropylethylamine (4.8 g). The temperature was raised to 50 to 55° C. and allowed to react for 5 hours. After the reaction was completed, the reaction solution was cooled to room temperature. Ethyl acetate (33.5 ml) and water (33.5 ml) were added and mixed. After mixing was completed, layers were separated. The organic layer was washed by adding water (33.5 ml), layers were separated and the organic layer was concentrated. Ethyl acetate (33.5 ml) was added to the obtained oil of (2R)-1-[3,5-bis(trifluoromethyl)benzoyl]-4-[2-[(2S)-2-(methoxymethyl)-morpholino]ethyl]-2-(3-hydroxy-4-methylbenzyl)piperazine to effect dissolution and then the solution was concentrated. The obtained concentrate was diluted with acetone (100 ml), clarified and filtered, and washed with acetone (34 ml). Concentrated hydrochloric acid (3.9 g) was added dropwise to the combined filtrate and washings at room temperature and crystallization was effected under ice-cooling for 8 hours. Crystals were collected by filtration, washed with acetone (33.5 ml), dried under reduced pressure and moistured to give (2R)-1-[3,5-bis(trifluoromethyl)benzoyl]-4-[2-[(2S)-2-(methoxymethyl)morpholino]ethyl]-2-(3-hydroxy-4-methyl-benzyl)piperazine dihydrochloride sesquihydrate (8.1 g, yield: 76.7%) in the form of white crystals.

Water content (Karl-Fischer method): 4.09% (Theoretical value for sesquihydrate: 3.85%)

Cl$^-$content (ion-chromatography method): 10.21% (Theoretical value for dihydrochloride: 10.08%)

Powder X-ray diffraction pattern: As shown in FIG. 1, specific peaks were observed around 4.8, 9.6, 14.4, 16.5, 19.0 and 22.4 (°) in powder X-ray diffraction values (2θ).

IR absorption spectrum (KBr method): As shown in FIG. 2, specific peaks were observed around 2927, 2544, 1636, 1279, 1135 and 682 (cm$^{-1}$).

(b) In the same manner as that in preceding section (a) except that isopropyl alcohol was used as a solvent for dilution and washing in place of acetone, (2R)-1-[3,5-bis (trifluoromethyl)benzoyl]-4-[2-[(2S)-2-(methoxymethyl)-morpholino]ethyl]-2-(3-hydroxy-4-methylbenzyl)piperazine dihydrochloride sesquihydrate was obtained in the form of white crystals (yield: 82.9%).

Formation of a dihydrochloride sesquihydrate with the same crystal form as that in the preceding section (a) was confirmed by powder X-ray diffraction pattern and infrared absorption spectrum.

(c) In the same manner as that in preceding section (a) except that ethyl acetate was used as a solvent for dilution and washing in place of acetone, (2R)-1-[3,5-bis(trifluoromethyl)benzoyl]-4-[2-[(2S)-2-(methoxymethyl)-morpholino] ethyl]-2-(3-hydroxy-4-methylbenzyl)piperazine dihydrochloride sesquihydrate was obtained in the form of white crystals (yield: 81.7%).

Formation of a dihydrochloride sesquihydrate with the same crystal form as that in the preceding section (a) was confirmed by powder X-ray diffraction pattern and infrared absorption spectrum.

INDUSTRIAL APPLICABILITY

Figure 1:
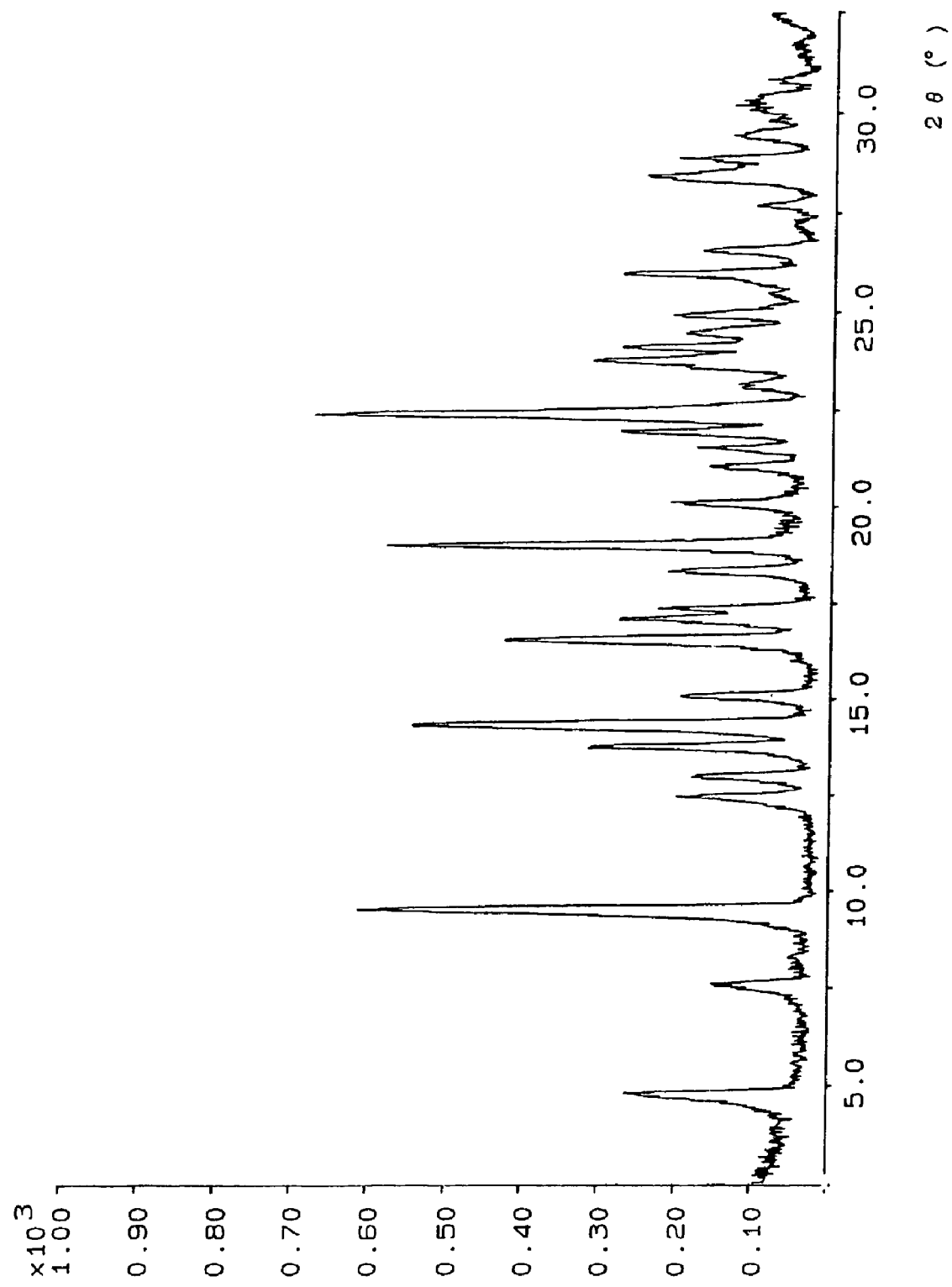
FIG. 1 shows the powder X-ray diffraction pattern of (2R)-1-[3,5-bis(trifluoromethyl)benzoyl]-4-[2-[(2S)-2-(methoxymethyl)morpholino]ethyl]-2-(3-hydroxy-4-methylbenzyl)piperazine dihydrochloride sesquihydrate.
Figure 2:
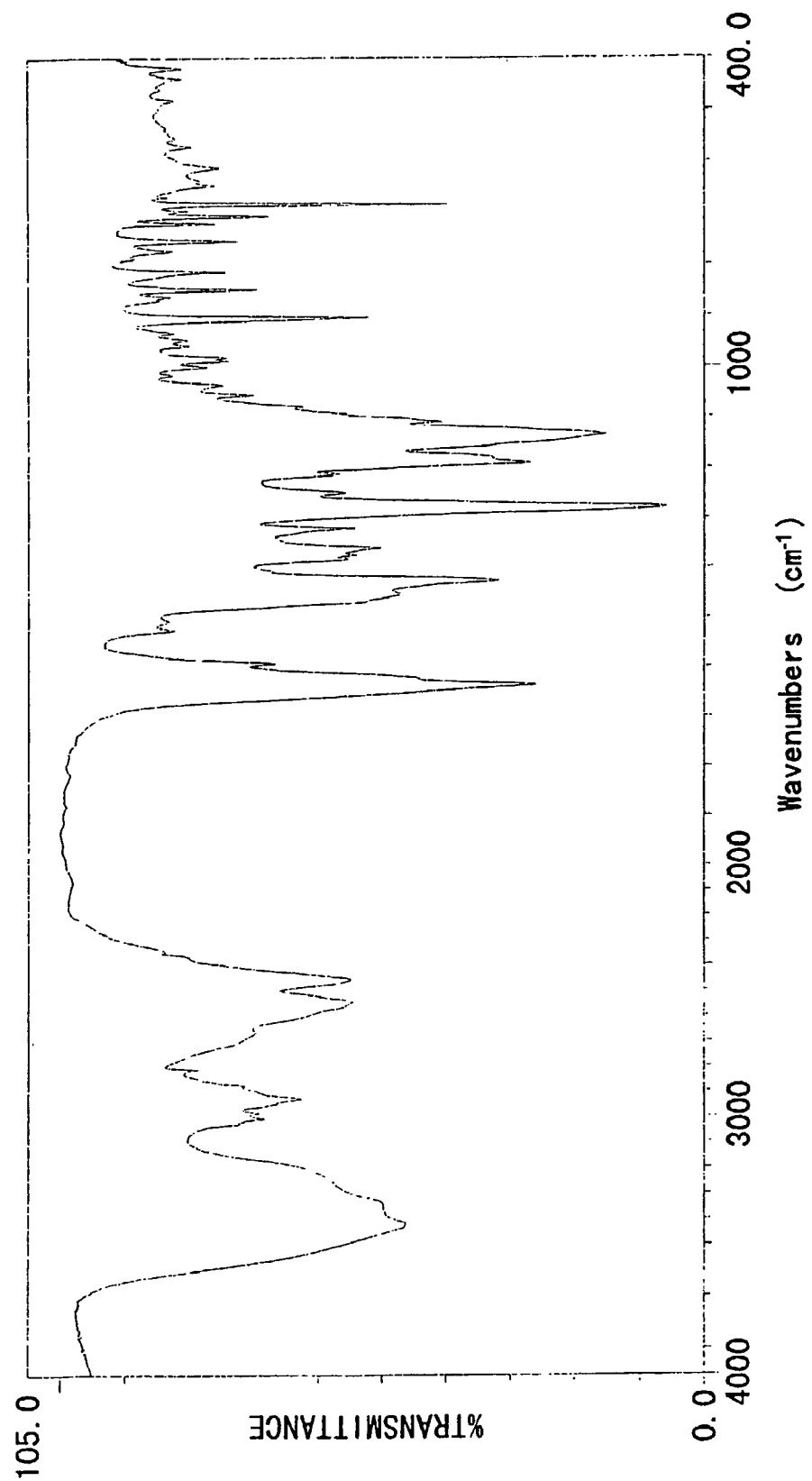
FIG. 2 shows the infrared absorption spectrum of (2R)-1-[3,5-bis(trifluoromethyl)benzoyl]-4-[2-[(2S)-2-(methoxymethyl)morpholino]ethyl]-2-(3-hydroxy-4-methylbenzyl)piperazine dihydrochloride sesquihydrate.

According to the invention, preparation of (2R)-1-[3,5-bis(trifluoromethyl)benzoyl]-4-[2-[(2S)-2-(methoxy-methyl)morpholino]ethyl]-2-(3-hydroxy-4-methylbenzyl)-piperazine dihydrochloride sesquihydrate with a high yield and in a good efficiency became possible.

The invention claimed is:

1. A process for preparing (2R)-1-[3,5-bis(trifluoromethyl)benzoyl]-4-[2-[(2S)-2-(methoxymethyl)morpholino] ethyl]-2-(3-hydroxy-4-methylbenzyl)piperazine dihydrochloride, which comprises:

(1) debenzylating (2R)-4-benzyl-1-[3,5-bis(trifluoromethyl)benzoyl]-2-(3-hydroxy-4-methylbenzyl)piperazine by chemical reduction with a hydride, a combination of metals or a metal compound with an organic acid or an inorganic acid to produce (2R)-1-[3,5-bis (trifluoromethyl)benzoyl]-2-(3-hydroxy-4-methylbenzyl)piperazine;

(2) reacting (2R)-1-[3,5-bis(trifluoromethyl)benzoyl]-2-(3-hydroxy-4-methylbenzyl)piperazine with (2S)-4-(2-chloroethyl)-2-(methoxymethyl)morpholine or a salt thereof in the presence of a base to produce (2R)-1-[3,5-bis(trifluoromethyl)benzoyl]-4-[2-[(2S)-2-(methoxymethyl)morpholino]ethyl]-2-(3-hydroxy-4-methylbenzyl)piperazine; and (3) converting the (2R)-1-[3,5-bis(trifluoromethyl)benzoyl]-4-[2-[(2 S)-2-(methoxymethyl)morpholino]ethyl]-2-(3-hydroxy-4-methylbenzyl)piperazine to its hydrochloride salt.

2. The process of claim 1, wherein the salt of (2S)-4-(2-chloroethyl)-2-(methoxymethyl)morpholine is an organic acid salt, an inorganic acid salt, an amino acid salt, an alkali metal salt, an alkaline earth metal salt or an ammonium salt.

3. The process of claim 1, wherein the base of step (2) is an alkali metal carbonate, an alkali metal bicarbonate, a tri(lower)alkylamine, pyridine, an N-(lower)-alkylmorpholine, a N,N-di(lower)alkylethylamine or a N,N-di(lower)alkylbenzylamine.

4. A process for preparing (2R)-1-[3,5-bis(trifluoromethyl)benzoyl]-4-[2-[(2S)-2-(methoxymethyl)morpholino]ethyl]-2-(3-hydroxy-4-methylbenzyl)piperazine dihydrochloride, which comprises:

(1) debenzylating (2R)-4-benzyl-1-[3,5-bis(trifluoromethyl)benzoyl]-2-(3-hydroxy-4-methylbenzyl)piperazine by reduction in the presence of a palladium catalyst and a formate salt to produce (2R)-1-[3,5-bis(trifluoromethyl)benzoyl]-2-(3-hydroxy-4-methylbenzyl)piperazine;

(2) reacting (2R)-1-[3,5-bis(trifluoromethyl)benzoyl]-2-(3-hydroxy-4-methylbenzyl)piperazine with (2S)-4-(2-chloroethyl)-2-(methoxymethyl)morpholine or a salt thereof in the presence of a N,N-di(lower)alkylethylamine base to produce (2R)-1-[3,5-bis(trifluoromethyl)benzoyl]-4-[2-[(2S)-2-(methoxymethyl)morpholino]ethyl]-2-(3-hydroxy-4-methylbenzyl)piperazine; and (3) converting the (2R)-1-[3,5-bis(trifluoromethyl)benzoyl]-4-[2-[(2S)-2-(methoxymethyl)morpholino]ethyl]-2-(3-hydroxy-4-methylbenzyl)piperazine to its hydrochloride salt.

5. The process of claim 4, wherein the temperature of the debenzylation reaction ranges from 40 to 600° C.

6. The process of claim 4, wherein the temperature of the reaction of step (2) ranges from 40 to 60° C.

7. The process of claim 6, wherein the reaction with base occurs in a solvent selected from the group consisting of water, an alcohol, acetone, dioxane, acetonitrile, chloroform, methylene chloride, ethylene chloride, tetrahydrofuran, ethyl acetate, N,N-dimethylformamide or pyridine.

8. The process of claim 5, wherein the reduction reaction occurs in a solvent selected from the group consisting of water, an alcohol, tetrahydrofuran, dioxane, toluene, methylene chloride, ethylene chloride, chloroform, N,N-dimethylformamide or N,N-dimethylacetamide.

9. The process of claim 1, wherein the temperature of the debenzylation reaction ranges from 40 to 60° C.

10. The process of claim 9, wherein the reduction reaction occurs in a solvent selected from the group consisting of water, an alcohol, tetrahydrofuran, dioxane, toluene, methylene chloride, ethylene chloride, chloroform, N,N-dimethylformamide or N,N-dimethylacetamide.

11. The process of claim 1, wherein the temperature of the reaction of step (2) ranges from 40 to 60° C.

12. The process of claim 11, wherein the reaction with base occurs in a solvent selected from the group consisting of water, an alcohol, acetone, dioxane, acetonitrile, chloroform, methylene chloride, ethylene chloride, tetrahydrofuran, ethyl acetate, N,N-dimethylformamide or pyridine.

* * * * *